US011367333B2

(12) United States Patent
Nakabayashi (10) Patent No.: US 11,367,333 B2
(45) Date of Patent: Jun. 21, 2022

(54) PERSONAL SAFETY VERIFICATION SYSTEM

(71) Applicants: SEKISUI HOUSE, LTD., Osaka (JP); E-SOLUTIONS, INC., Tokyo (JP)

(72) Inventor: Yoshiki Nakabayashi, Osaka (JP)

(73) Assignees: SEKISUI HOUSE, LTD., Osaka (JP); E-SOLUTIONS, INC., Tokyo (JP)

( * ) Notice: Subject to any disclaimer, the term of this patent is extended or adjusted under 35 U.S.C. 154(b) by 0 days.

(21) Appl. No.: 17/441,148

(22) PCT Filed: Mar. 22, 2019

(86) PCT No.: PCT/JP2019/012020
§ 371 (c)(1),
(2) Date: Sep. 20, 2021

(87) PCT Pub. No.: WO2020/194370
PCT Pub. Date: Oct. 1, 2020

(65) Prior Publication Data
US 2022/0148405 A1 May 12, 2022

(30) Foreign Application Priority Data
Mar. 22, 2019 (JP) .............................. JP2019-053999

(51) Int. Cl.
*G08B 21/04* (2006.01)
*A61B 5/11* (2006.01)
(52) U.S. Cl.
CPC ........ *G08B 21/0461* (2013.01); *A61B 5/1113* (2013.01); *G08B 21/0469* (2013.01); *G08B 21/0476* (2013.01)
(58) Field of Classification Search
CPC ............ G08B 21/0461; G08B 21/0469; G08B 21/0476; A61B 5/1113
See application file for complete search history.

(56) References Cited

U.S. PATENT DOCUMENTS 6,603,401 B1   8/2003   Ueyama
9,412,255 B1 *  8/2016  Frost .................. G08B 21/0423
(Continued)

FOREIGN PATENT DOCUMENTS

JP   2002-269662   9/2002
JP   2015-026146   2/2015
(Continued)

OTHER PUBLICATIONS

International Preliminary Report on Patentability for PCT/JP2019/012020, dated Oct. 7, 2021, 7 pages.
(Continued)

*Primary Examiner* — Curtis J King
(74) *Attorney, Agent, or Firm* — Casimir Jones, SC; Robert A. Goetz (57) ABSTRACT

The present invention includes: a first sensor (111a) which is provided in a house (10) and which detects, without contact, at least the heart rate and the respiratory rate of a resident (15); an anomaly determining section (201) which detects significant difference in the heart rate and the respiratory rate from a normal state; a communication section (210) which carries out communication between an operator (25) and a resident (15) for verifying safety; an arrival information presenting section (206) which presents, to the operator (25), the arrival of an emergency medical worker (35) at a house (10) in response to a dispatching request by the operator (25); and a remote unlocking section (203) which carries out emergency unlocking of a lock of the house (10) in accordance with an instruction of the operator (25).

7 Claims, 4 Drawing Sheets (56) References Cited

U.S. PATENT DOCUMENTS

| | | | |
|---|---|---|---|
| 10,825,318 B1* | 11/2020 | Williams | G06N 3/0454 |
| 2003/0069002 A1* | 4/2003 | Hunter | G08B 25/016 |
| | | | 455/567 |
| 2006/0089538 A1* | 4/2006 | Cuddihy | A61B 5/0002 |
| | | | 600/595 |
| 2007/0008154 A1* | 1/2007 | Albert | G08B 21/0453 |
| | | | 340/573.1 |
| 2013/0245389 A1* | 9/2013 | Schultz | A61B 5/0002 |
| | | | 600/301 |
| 2017/0169699 A1 | 6/2017 | Will et al. | |
| 2018/0103874 A1* | 4/2018 | Lee | A61B 5/6823 |
| 2019/0087510 A1* | 3/2019 | Rexach | G05B 19/042 |
| 2020/0085370 A1* | 3/2020 | Hill | A61B 5/0816 |
| 2020/0378758 A1* | 12/2020 | Yang | A61B 5/7267 |
| 2021/0256829 A1* | 8/2021 | Ten Kate | G08B 29/16 |

FOREIGN PATENT DOCUMENTS

| | | |
|---|---|---|
| JP | 2015-158892 | 9/2015 |
| JP | 2017-153850 | 9/2017 |
| JP | 2017-191548 | 10/2017 |
| JP | 2018-072886 | 5/2018 |
| WO | WO 01/004441 | 1/2001 |

OTHER PUBLICATIONS

International Search Report for PCT/JP2019/012020, dated Apr. 16, 2019, 2 pages.
Office Action for GB Patent Application No. 2113504.1, dated Nov. 9, 2021, 3 pages.

* cited by examiner

PERSONAL SAFETY VERIFICATION SYSTEM

TECHNICAL FIELD

The present invention relates to a safety verification system that is capable of determining an anomaly of a resident and requesting emergency help.

BACKGROUND ART

There are still many cases of acute diseases and accidents occurring at one's home. In recent years, aging society where an increasing number of people are living alone is making it increasingly important how accidents and acute diseases at one's home are handled.

Under the circumstances, Patent Literature 1, for example, discloses a building in which a sensor is provided in a living space in which a resident lives, and, when the sensor detects an abnormal state that is set in advance, notification for prompting the verification of the safety of the resident is sent out.

Patent Literature 2 discloses a living body monitoring system that determines an abnormal state by analyzing the activity status of a living body on the basis of the detection result of a sensor that detects the movement of the living body and the detection result of a sensor that detects the state of a living environment in which the living body lives.

Patent Literature 3 discloses an electronic lock control system that controls locking and unlocking of an electronic lock, the electronic lock control system being configured to transmit an unlock command to the electronic lock, in conjunction with communication to a person/place of contact set in advance.

CITATION LIST

Patent Literature

[Patent Literature 1]
Japanese patent application publication, No. 2015-26146 (Publication Date: Feb. 5, 2015)
[Patent Literature 2]
Japanese patent application publication, No. 2017-153850 (Publication Date: Sep. 7, 2017)
[Patent Literature 3]
PCT International Publication, No. 01/004441 (Publication Date: Jan. 18, 2001)

SUMMARY OF INVENTION

Technical Problem

However, the above conventional techniques cannot be said to be sufficient. There is room for further operation in order to precisely determine an anomaly of a resident and handle the occurrence of the anomaly more safely, more reliably, and quickly.

An aspect of the present invention has been made in view of the problem, and the object of the present invention is to achieve a safety verification system that precisely determines an anomaly of a resident and handles the occurrence of the anomaly more safely, more reliably, and quickly.

Solution to Problem

In order to attain the above object, a safety verification system in accordance with an aspect of the present invention includes: at least one first sensor which is provided in a residential building and which detects, without contact, at least a heart rate and a respiratory rate of a resident of the residential building; a storage section which stores sensing data of the at least one first sensor; a detecting section which makes a comparison between the sensing data stored in the storage section and new sensing data of the at least one first sensor for detecting significant differences at least in the heart rate and the respiratory rate of the resident from a normal state; a communication section which carries out communication between the residential building and a facility away from the residential building; a notifying section which is provided in the facility and which notifies an operator in the facility of an occurrence of an anomaly via the communication section; an alerting section which causes, via the communication section, the notifying section to raise an alert when the detecting section has detected the significant differences; a safety verifying section which carries out, via the communication section, communication between the operator and the resident for verifying safety; a physiological information presenting section which is provided in the facility and which obtains at least the significant differences via the communication section and present at least the significant differences to the operator; an arrival information presenting unit which presents, to the operator, arrival of an emergency medical worker at the residential building in response to a dispatching request by the operator; and an unlocking unit which carries out, in response to an unlocking request by the operator, emergency unlocking of a lock that is provided at an entrance of the residential building.

Advantageous Effects of Invention

With an aspect of the present invention, it is advantageously possible to precisely determine an anomaly of a resident and handle the occurrence of the anomaly more safely, more reliably, and quickly.

DESCRIPTION OF EMBODIMENTS

Embodiment 1

The following description will discuss, in detail, an embodiment of the present invention with reference to the drawings. Although the embodiment discussed in the following description includes various limitations that are preferable from a technical perspective for putting the present invention into practice, the technical scope of the present invention is not limited to the embodiment below or the examples in the drawings.

Overview

Figure 1:
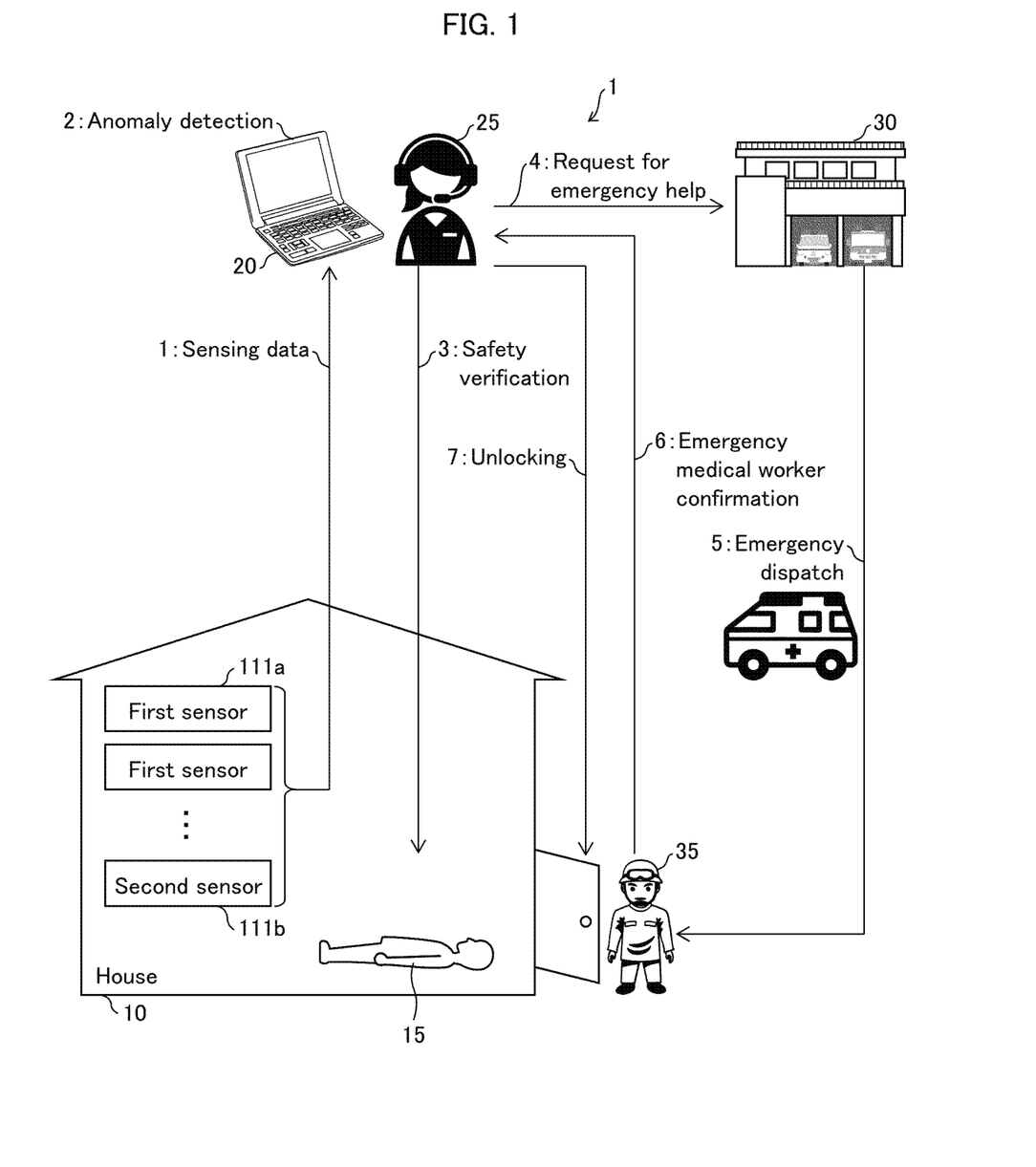
FIG. 1 is a view illustrating an overview of a safety verification system in accordance with an embodiment of the present invention.

An overview of a safety verification system 1 in accordance with Embodiment 1 will be described below with reference to FIG. 1. FIG. 1 is a view illustrating the overview of the safety verification system 1. As illustrated in FIG. 1, the safety verification system 1 includes: a house (residential building) 10 in which a resident 15 lives; and a management device 20 of a management company. The house 10 is provided with one or more sensors 111 such that sensing data of the sensors 111 can be transmitted to the management device 20 of the management company, via a wired or wireless connection. Specifically, the house 10 and the management device 20 can communicate with each other via an electric telecommunication line (such as the Internet, a dedicated line, or a telephone line). The sensors 111 includes: a first sensor 111a that detects the physiological information (heart rate, respiratory rate) of the resident 15; and a second sensor 111b that detects the activity of the resident 15. Hereinafter, when it is not necessary to distinguish between the first sensor 111a and the second sensor 111b, these will be simply referred to as "sensor(s) 111".

The management device 20 is provided at a place away from the house 10, for example, at the location of the management company (such as a service provider or a homebuilder). The house 10 can be one single residential building or one unit of a multi-unit residential building.

According to the safety verification system 1 in accordance with Embodiment 1, the various sensors 111 provided in the house 10 sense the state of the resident 15, and transmit sensing data to the management device 20. The management device 20 analyzes the received sensing data to determine whether or not the resident 15 has experienced an anomaly, more specifically, whether or not the resident has fallen, and, if the resident has fallen, whether or not the resident remains in a fallen state. If the management device 20 has detected that the resident remains in the fallen state and the heart rate, the respiratory rate, and the like are different from a normal state (there are significant differences), the management device 20 determines that there is an anomaly. If the management device 20 has determined that there is an anomaly, the management device 20 notifies an operator 25 that there is an anomaly. The operator 25 verifies with the house 10 the safety of the resident 15, and, if the safety of the resident 15 cannot be confirmed, requests an emergency medical service 30 to provide emergency help. When an emergency medical worker 35 has arrived at the house 10, the operator 25 confirms, by a camera 130 installed at the house 10, that it is the emergency medical worker 35 who has arrived, and unlocks the entrance door of the house 10 by remote operation.

The safety verification system 1 in accordance with Embodiment 1 is thus configured so that, if the resident 15 has fallen in the house 10 and is in a state different from the normal state, the operator 25 verifies the safety, and, if the safety cannot be confirmed, requests emergency help, and, when the operator 25 confirms that it is the emergency medical worker 35 who has arrived at the house 10, unlocks the lock that is provided at the entrance of the house 10. This makes it possible to handle an anomaly of the resident 15 safely, reliably, and quickly.

According to Embodiment 1, it is determined whether or not the resident 15 is in the fallen state, and, if the resident 15 is in the fallen state, it is determined whether or not the heart rate and the respiratory rate are abnormal. However, it is alternatively possible to omit the determination of the fallen state and determine an anomaly of the resident 15 on the basis of significant differences in the heart rate and respiratory rate from the normal state.

[Details of House 10 and Management Device 20]

Figure 2:
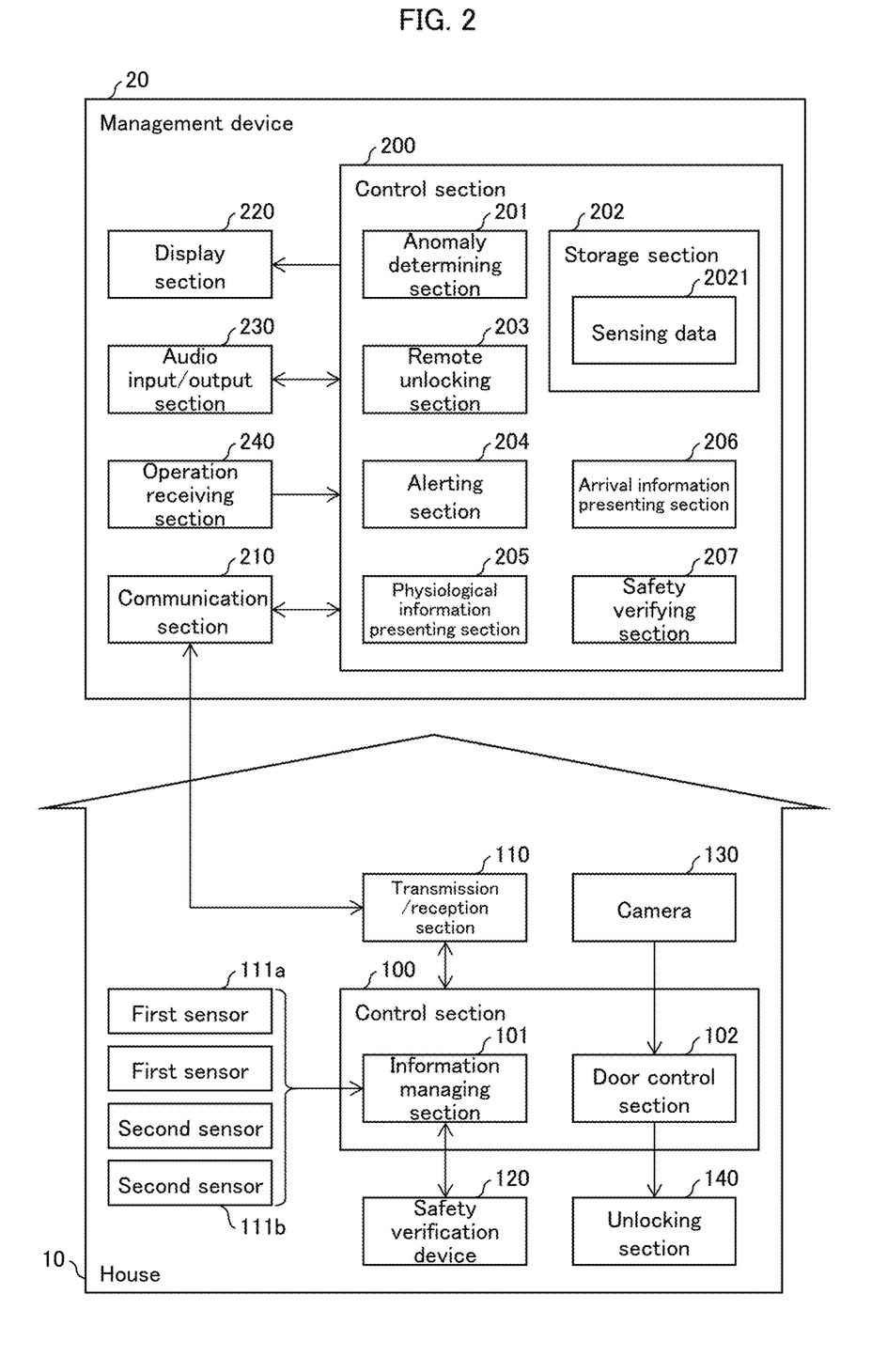
FIG. 2 is a functional block diagram of a house and a management device which are included in the safety verification system.

The details of the house 10 and the management device 20 will be described next with reference to FIG. 2. FIG. 2 is a functional block diagram of the house 10 and the management device 20.

As illustrated in FIG. 2, the house 10 includes a control section 100, a transmission/reception section 110, a safety verification device 120, a camera (image capturing section) 130, an unlocking section 140, and the sensors 111.

The sensors 111 are one or more non-wearable sensors provided in each room of the house 10. The sensors 111 include: a first sensor 111a that is capable of detecting the physiological information and the like of the resident 15 without contact; and a second sensor 111b that is capable of detecting the activity of the resident 15 without contact.

Providing one or more radio wave sensors as the first sensor 111a in each room of the house 10 makes it possible to sense the respiratory rate, the heart rate, and the like of the resident 15. Although the details will be omitted because it is a known technique to use a radio wave sensor to sense the physiological information (respiratory rate, heart rate) of a living body, it is possible to detect physiological information by irradiating a detection target with radio waves, detecting reflected waves, and analyzing a detected signal (see, for example, Japanese Patent Application Publication, Tokukai, No. 2017-153850, Japanese Patent Application Publication, Tokukai, No. 2009-060989, and Japanese Patent Application Publication, Tokukai, No. 2000-83927).

Examples of the second sensor 111b encompass a human sensor that detects the activity of the resident 15 and an environment sensor that can detect the state of the house 10. Examples of the human sensor encompass a pressure sensor, an infrared sensor, an image sensor, and an opening/closing sensor. Examples of the environment sensor encompass a sound sensor, a temperature sensor, and a luminance sensor.

Providing a pressure sensor at, for example, the floor of the house 10 makes it possible to detect a pressure that is applied by the body weight or the like of the resident 15. This makes it possible to detect that the resident 15 is lying down in an unsuitable place, that is, the resident 15 has fallen, and makes it possible to detect the movement of the resident 15 in the house 10.

Providing a human sensor at, for example, a door of the house 10 makes it possible to detect that the resident 15 has passed by in the house 10.

Each of the sensors 111 transmits, to an information managing section 101 of the control section 100, sensing data that shows a sensing result.

The control section 100 controls each device provided in the house 10, and includes the information managing section 101 and a door control section 102. The control section 100 stores, for example, data and various control programs to be executed by a CPU. The control section 100 carries out various processes according to the programs.

The information managing section 101 obtains sensing data from the sensors 111, and transmits the sensing data to the management device 20 via the transmission/reception section 110.

The door control section 102 obtains an image by the camera 130 that is provided at the entrance of the house 10, and transmits the image to the management device 20 via the transmission/reception section 110. In response to an instruction from the management device 20, the door control section 102 also controls the unlocking section 140 so as to unlock the entrance door of the house 10.

The transmission/reception section 110 carries out communication between the house 10 and the management device 20.

In response to the instruction from the management device 20, the safety verification device 120 verifies the safety of the resident 15. The safety verification device 120 can be, for example, a telephone or a device including a speaker and a microphone. If the safety verification device 120 is a telephone, it is possible to verify the safety of the resident 15 by ringing the telephone by the operation of the operator 25. If the safety verification device 120 is a device including a speaker and a microphone, it is possible to verify the safety of the resident 15 by outputting a calling voice of the operator 25 from the speaker and picking up a reply of the resident 15 with the microphone. If the safety verification device 120 includes a speaker and a microphone, the safety verification device 120 is preferably provided in each room of the house 10.

The camera 130 is provided at the entrance of the house 10 to capture an image of a visitor. The image captured by the camera 130 is transmitted to the door control section 102. For example, when an emergency medical worker 35 has arrived, the camera 130 captures an image of the emergency medical worker 35, and the captured image is transmitted to the management device 20 and is displayed by a display section (notifying section, presenting section) 220. By confirming the captured image captured by the camera 130 and displayed by the display section 220, the operator 25 can confirm that it is the emergency medical worker 35 who has arrived at the house 10

The unlocking section 140 unlocks the entrance door of the house 10 in response to an instruction of the door control section 102. For example, if the operator 25 is to give an unlock instruction, the operator 25 operates an operation receiving section 240 to transmit the unlock instruction to the house 10. The door control section 102 of the control section 100, which has received the unlock instruction, controls the unlocking section 140 so as to unlock the entrance door of the house 10.

As illustrated in FIG. 2, the management device 20 also includes a control section 200, a communication section (transmitting section) 210, the display section 220, an audio input/output section 230, and the operation receiving section 240.

The control section 200 includes an anomaly determining section (fall determining section, detecting section) 201, a storage section 202, a remote unlocking section 203, an alerting section 204, a physiological information presenting section 205, and an arrival information presenting section 206. The control section 200 stores, for example, data and various control programs to be executed by a CPU. The control section 200 carries out various processes according to the programs.

The anomaly determining section 201 analyzes sensing data of the sensors 111, which has been transmitted from the house 10, and determines the presence/absence of an anomaly of the resident 15. More specifically, the anomaly determining section 201 uses the sensing data of the first sensor, among the sensors 111, which is capable of sensing the activity of the resident, to determine, for example, whether or not the resident has fallen and is in a fallen state. If the resident is in the fallen state, the anomaly determining section 201 uses the sensing data of the second sensor, among the sensors 111, which is capable of sensing the heart rate, the respiratory rate, and the like of the resident, to determine, for example, whether or not there are significant differences in the heart rate, the respiratory rate, and the like of the resident from the normal state. If the significant differences are detected, the anomaly determining section 201 determines that the resident has experienced the anomaly. The determination of an anomaly is carried out by, for example, storing obtained sensing data in the storage section 202 (as sensing data 2021) and determining whether or not significant differences between the stored sensing data and newly obtained sensing data can be identified. Alternatively, it is possible to set a threshold for sensing data, and, if the sensing data exceeds the threshold, determine that there is an anomaly. In such a case, the threshold can be stored in the storage section 202. Alternatively, the determination of an anomaly can be carried out with use of a learning model in which normal data and anomaly data are used as learning data. In addition, as data for determining an anomaly, the storage section 202 can store, for example, normal physiological information (such as: data pertaining to the physique such as the body height and the body weight; and data of the heart rate) and normal activity information (such as information regarding the activity pattern for certain days of the week and certain time of the day) of the resident 15. Using these pieces of information makes it possible to set a standard for determining the presence/absence of an anomaly of the resident 15.

In accordance with the operation of the operator 25, the remote unlocking section 203 transmits, to the house 10, an instruction for remotely unlocking the house 10. The remote unlocking is carried out such that the unlocking section 140 is notified of the instruction of the remote unlocking section 203 via the communication section 210, and the unlocking section 140 unlocks the entrance door of the house 10. Thus, the remote unlocking section 203, the communication section 210, and the unlocking section 140 constitute an unlocking unit.

Unlocking of the lock provided at the house 10 is not limited to a remote operation of the operator 25. For example, if the lock provided at the house 10 can be unlocked with a password, the remote unlocking section 203 can transmit a one-time password to a mobile terminal carried by an emergency medical worker 35, and the emergency medical worker 35 can use the password to unlock the lock.

In Embodiment 1, remote unlocking by the operation of an operator 25 and unlocking with the use of a one-time password by an emergency medical worker 35 are also referred to as emergency unlocking. Emergency unlocking means unlocking that is different from normal unlocking. Normal unlocking includes unlocking that is usually carried out by the resident 15. Examples of the normal unlocking encompass unlocking with a key, unlocking with a mobile terminal, and unlocking with a password. In contrast to these examples of usual unlocking, emergency unlocking means unusual unlocking such as remote unlocking by the operation of an operator 25 and unlocking with use of a one-time password.

When the anomaly determining section 201 determines that a resident has experienced an anomaly, the alerting section 204 causes the display section 220 to display, for example, such indication so as to notify the operator 25. The alerting section 204 can notify the operator 25 of an anomaly of the resident by turning on a red lamp (not illustrated) or the like or by causing the audio input/output section 230 to output an alerting sound.

The physiological information presenting section 205 obtains, from the house 10 via the communication section 210, the physiological information of the resident 15 detected by the first sensor 111a, and displays the physiological information on the display section 220, so as to present the physiological information to the operator 25. Thus, the first sensor 111a, the communication section 210, the physiological information presenting section 205, and the display section 220 constitute a physiological information presenting unit that presents the physiological information of the resident 15 to the operator 25.

The arrival information presenting section 206 obtains, from the house 10 via the communication section 210, an image (still image, moving image) of the house 10 captured by the camera 130, and displays the image on the display section 220. The camera 130 is provided at the entrance of the house 10 so as to be able to capture an image of a visitor. This allows the operator 25 to verify, by viewing the image (video), whether or not it is an emergency medical worker 35 who has arrived at the house 10. Thus, the camera 130, the communication section 210, the arrival information presenting section 206, and the display section 220 constitute an arrival information presenting unit by which the operator 25 verifies whether or not it is an emergency medical worker 35 who has arrived at the house 10.

If it is possible to identify the location of an emergency medical worker 35 with use of, for example, GPS information of a mobile terminal or the like carried by the emergency medical worker 35, the arrival information presenting section 206 can use the GPS information to determine that the emergency medical worker 35 has arrived at the house 10 and present the arrival of the emergency medical worker 35 to the operator 25.

The safety verifying section 207 verifies the safety of the resident 15. More specifically, the safety verifying section 207 verifies the safety of the resident 15 through the communication section 210 in accordance with an instruction of the operator 25. The safety can be verified such that a calling voice of the operator 25 from the audio input/output section 230 is transmitted to the safety verification device 120 of the house 10 via the communication section 210 and is outputted from the speaker of the safety verification device 120. The reply from the resident 15 is picked up by the microphone of the safety verification device 120 and is outputted from the audio input/output section 230 via the communication section 210. This allows the operator 25 to verify the safety of the resident 15.

Alternatively, it is possible that a camera is provided within the house 10, and the safety verifying section 207 obtains, via the communication section 210, an image captured by the camera and displays the image on the display section 220 so that the operator 25 can verify the safety of the resident 15.

The communication section 210 carries out communication between the management device 20 and the house 10.

The display section 220 is a display device that presents, to the operator 25, the status of sensing data and the presence/absence of an anomaly. If the anomaly determining section 201 determines that there is an anomaly, the display section 220 displays, in accordance with an instruction of the alerting section 204, information indicating that it has been determined that there is the anomaly.

The audio input/output section 230 is for inputting and outputting a voice, and, for example, includes a microphone and a speaker. When the operator 25 is to verify the safety of the resident 15, the operator 25 speaks to the resident 15 via the microphone and confirms the reply of the resident 15 with use of the speaker. This makes it possible to verify the safety of the resident 15.

The audio input/output section 230 can also have the function of a transmitting/receiving part of a telephone. Specifically, it is possible that the management device 20 has the function of a telephone so that the operator 25 transmits/receives audio via the audio input/output section 230. For example, when a request for emergency help is to be made, it is possible to make the request via the audio input/output section 230.

The operation receiving section 240 receives an operation on the management device 20, and is, for example, a keyboard and a mouse. It is possible to configure the display section 220 and the operation receiving section 240 integrally such as a case of a touch panel.

It is possible that the safety of the resident 15 is verified through an operation on the operation receiving section 240. For example, it is possible that clicking a safety verification button displayed on the display section 220 with a mouse or the like causes the safety verification device 120 of the house 10 to output a voice for verifying the safety of the resident 15.

As has been described, the safety verification system 1 in accordance with Embodiment 1 includes: the first sensor 111a which is provided in the house 10 and which detects that the resident 15 has fallen in the house 10 and detect the presence/absence of a subsequent movement of the resident 15 who has fallen; the anomaly determining section 201 which, on the basis of the sensing data of the first sensor 111a, determines whether or not the resident 15 is in a fallen state; the second sensor 111b which is provided in the house 10 and which detects the heart rate and the respiratory rate of the resident 15 in the fallen state; the anomaly determining section 201 which makes a comparison between the sensing data of the second sensor 111b and a specified numerical value for detecting significant differences in heart rate and respiratory rate of the person in the fallen state from a normal state; the display section 220 which is provided in the facility away from the house 10 and which notifies the operator 25 in the facility of the occurrence of an anomaly; the alerting section 204 which causes the display section 220 to raise an alert when the anomaly determining section 201 has detected the significant differences; the communication section 210 and the transmission/reception section 110 which carry out communication between the operator 25 and the resident 15 in the house 10 for verifying safety; the display section 220 which is provided in the facility and which obtains the sensing data of the first sensor 111a and present the sensing data to the operator 25; the camera 130 which is provided at the house 10 and which captures an image of an emergency medical worker who has arrived at the entrance of the house 10 in response to a dispatching request by the operator 25; the display section 220 which obtains the image captured by the camera 130 and displays the image to the operator 25; and the remote unlocking section 203 which unlocks, by the operation of the operator 25, a lock that is provided at the entrance of the house 10.

[Flow of Process of Safety Verification System 1]

Figure 3:
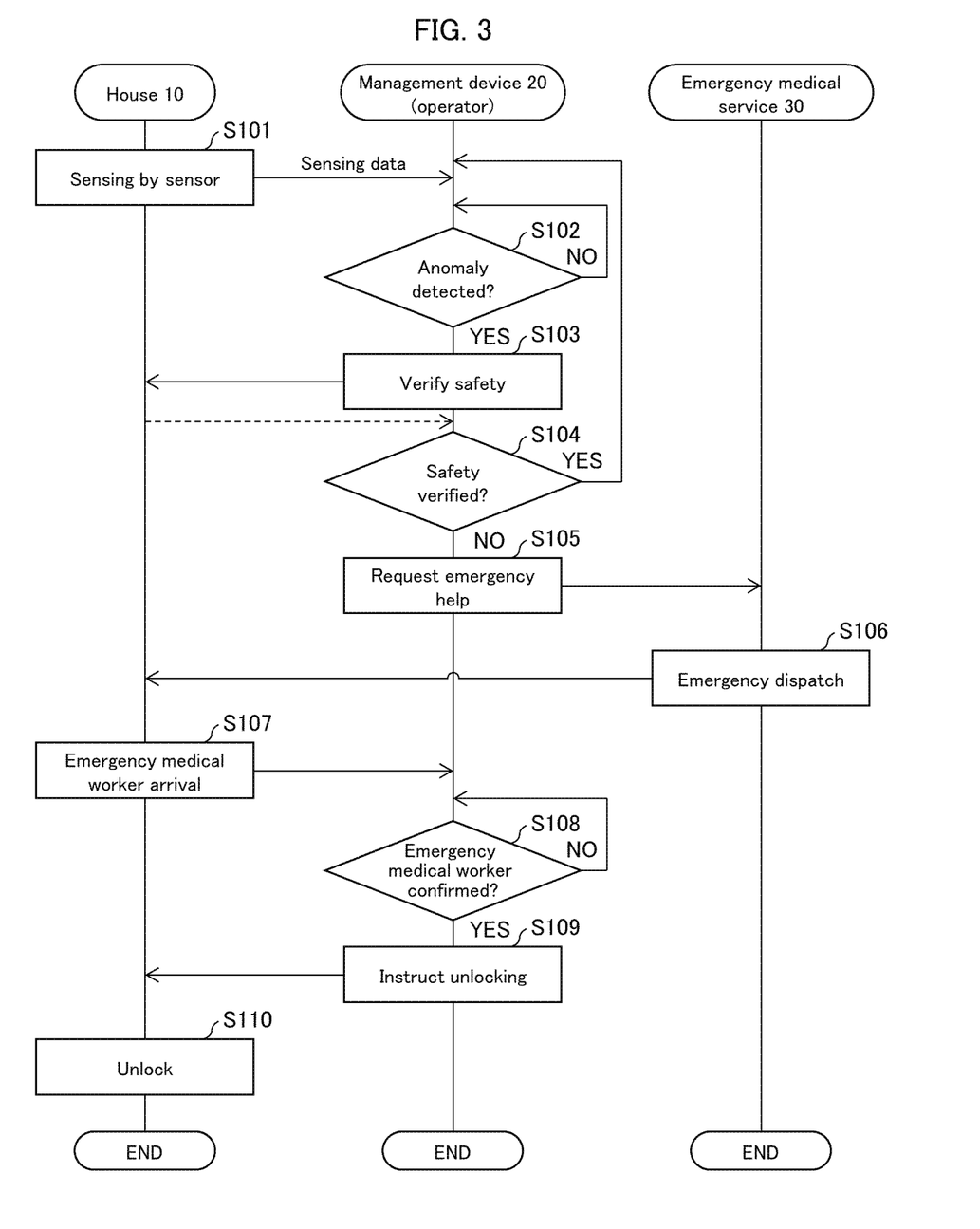
FIG. 3 is a flowchart illustrating the flow of the process of the safety verification system.

The flow of the process of the safety verification system 1 will be described next with reference to FIG. 3. FIG. 3 is a flowchart illustrating the flow of the process of the safety verification system 1.

As illustrated in FIG. 3, in the safety verification system 1, the sensors 111 provided in the house 10 carry out sensing (S101; sensing step), and the information managing section 101 transmits the sensing data to the management device 20. In the management device 20, the sensing data is stored in the storage section 202 (storing step). The sensors 111 can carry out sensing constantly or at predetermined intervals. For quickly detecting an anomaly of the resident 15, it is preferable to constantly carry out sensing.

In the management device 20 which has obtained the sensing data, the anomaly determining section 201 determines the presence/absence of an anomaly in the sensing data (S102). For example, on the basis of the sensing data of the second sensor 111b, the anomaly determining section 201 determines whether or not the resident 15 is a fallen state. If the anomaly determining section 201 has determined that the resident 15 is in the fallen state, the anomaly determining section 201, on the basis of the sensing data of the first sensor 111a, determines whether or not significant differences in the heart rate and the respiratory rate of the resident 15 from the normal state can be identified (detecting step). If the anomaly determining section 201 has identified the significant differences in the heart rate and the respiratory rate of the resident 15 from the normal state, the anomaly determining section 201 determines that the resident 15 has experienced an anomaly.

If the anomaly determining section 201 has determined that there is an anomaly, that is, if an anomaly in the sensing data has been detected (YES in S102), the operator 25 is notified that there has been an anomaly (alerting step), and the operator 25 verifies the safety of the resident 15 (S103; safety verifying step). The operator 25 verifies the safety by speaking to the resident 15. In addition, on the basis of the sensing data of the first sensor 111a, the operator 25 can verify whether or not the resident 15 is motionless in the fallen state. If the safety verification result confirms the safety of the resident 15 (YES in S104), the process returns to the step S101. If, in contrast, the safety of the resident 15 cannot be confirmed (NO in S104), the operator 25 requests the emergency medical service 30 to provide emergency help (S105). An emergency medical worker 35 is then dispatched by the emergency medical service 30 (S106). When the emergency medical worker 35 arrives at the house 10 of the resident 15 (S107), a door phone button is pressed, and the camera 130 provided at the house 10 captures an image of the visitor. Then, the captured image is transmitted to the management device 20. With the image captured by the camera 130, the operator 25 confirms that it is the emergency medical worker 35 who has arrived at the house 10 (S108; arrival information presenting step). It is possible that the transmission of images captured by the camera 130 to the management device 20 starts from when the anomaly determining section 201 determines that there is an anomaly. Alternatively, it is possible that an image captured by the camera 130 is transmitted to the management device 20 by the operation of the operator 25 in response to the determination of the presence of an anomaly. In addition, the transmission of images captured by the camera 130 to the management device 20 can end when the lock provided at the house 10 is unlocked by the remote operation by the operator 25.

If it is confirmed that the emergency medical worker has arrived (YES in S108), the operator 25 transmits, from the management device 20 to the house 10, an instruction for unlocking the entrance door of the house 10 (S109). The door control section 102 of the house 10, which has received the unlock instruction from the management device 20, controls the unlocking section 140 so as to unlock the entrance door of the house 10 (S110; unlocking step).

With this configuration, it is possible to quickly send an emergency medical worker 35 to the resident 15 when the resident 15 experiences an anomaly.

The above description discussed the configuration in which the management device 20 includes the anomaly determining section 201. Alternatively, the process of the anomaly determining section 201 can be carried out within the house 10. Specifically, it is possible that the control section 100 of the house 10 includes an anomaly determining section and a storage section that stores sensing data, and the anomaly determining section carries out a function similar to that of the anomaly determining section 201.

The above description discussed the configuration in which the operator 25 verifies the safety of the resident 15 and requests emergency help. Alternatively, artificial intelligence (AI) instead of the operator 25 can verify the safety of the resident 15 and request emergency help.

Embodiment 2

The following description will discuss another embodiment of the present invention. For convenience of description, members having functions identical to those of the members described in the above embodiment are assigned the same reference numerals, and descriptions thereof will not be repeated.

Figure 4:
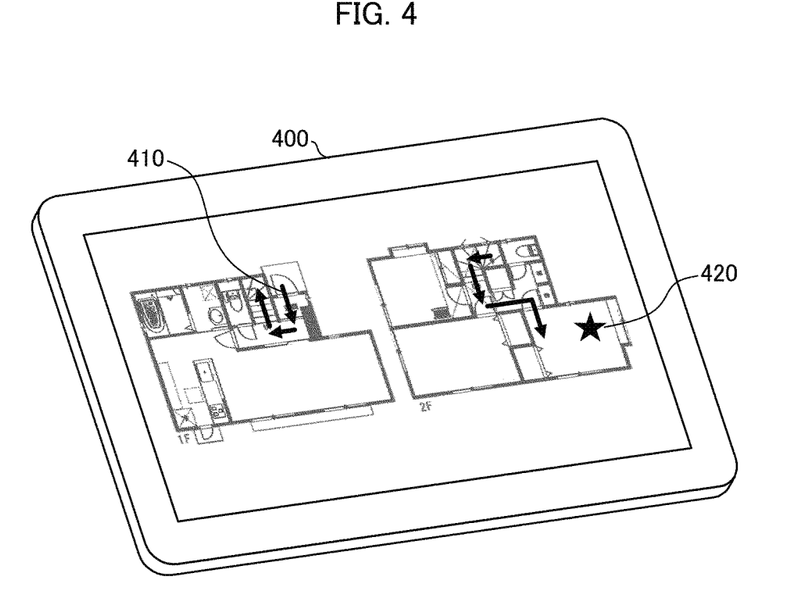
FIG. 4 is a view showing an example of guidance information to be presented to an emergency medical worker in another embodiment of the present invention.

According to Embodiment 2, an emergency medical worker 35 carries a mobile terminal (terminal) 400, and the mobile terminal 400 presents guidance information which guides to the location of a resident 15 in a house 10. Even when the emergency medical worker 35 has arrived at the house 10 of the resident 15, the emergency medical worker 35 still needs to find out where in the house 10 the resident 15 is located. If the situation is urgent, consuming time to search for the resident may lead to serious consequences. According to Embodiment 2, therefore, the mobile terminal 400 carried by the emergency medical worker 35 presents guidance information which shows the location of the resident 15 in the house 10. This makes it possible to quickly guide the emergency medical worker 35 to the location of the resident 15, and therefore makes it possible to reduce the amount of time wasted in searching for the resident.

FIG. 4 shows an example of guidance information. In the example shown in FIG. 4, the mobile terminal 400 shows a floor plan of the house 10 and arrows that guide from an entrance 410 through a location 420 of the resident 15. This allows the emergency medical worker 35 to recognize, at a glance, the location of the resident 15.

The guidance information can be generated by determining the location of the resident 15 on the basis of sensing data, provided that the floor plan of the house 10 is stored in the management device 20 in advance. Transmitting the guidance information from the management device 20 to the mobile terminal 400 allows the mobile terminal 400 to present the guidance information.

More specifically, a storage section 202 of the management device 20 stores diagram data that shows the floor plan of the house 10 and shows locations (rooms) where respective first sensors 111a are provided. The management device 20 includes a guidance information generating section that generates the guidance information from (i) the location of a first sensor 111a which, based on the sensing data of the first sensors 111a, corresponds to the room where the resident 15 has fallen and (ii) the floor plan. The guidance information is transmitted, via a communication section 210, to the mobile terminal 400 carried by the emergency medical worker 35.

As has been described, a safety verification system 1 in accordance with Embodiment 2 is configured so that the first sensors 111a are provided in the respective rooms of the house 10, the safety verification system including: the storage section which stores diagram data that shows the floor plan of the house 10 and shows the arrangement of the first sensors 111a; and the communication section 210 which transmits, to the mobile terminal 400 carried by the emergency medical worker 35, guidance information that is based on the sensing data of the first sensors 111a and on the diagram data and that guides to the room where the resident 15 in the fallen state is located. In addition, the guidance information can be indicative, on the floor plan of the house 10, of a route from the entrance of the house 10 to the location of the resident 15 in the fallen state.

[Software Implementation Example]

Control blocks of included in the safety verification system 1 (particularly, the information managing section 101 and the door control section 102 of the control section 100, and the anomaly determining section 201 included in the control section 200) can be realized by a logic circuit (hardware) provided in an integrated circuit (IC chip) or the like or can be alternatively realized by software.

In the latter case, the safety verification system 1 includes a computer that executes instructions of a program that is software realizing the foregoing functions. The computer, for example, includes at least one processor and at least one computer-readable storage medium storing the program. An object of the present invention can be achieved by the processor of the computer reading and executing the program stored in the storage medium. Examples of the processor encompass a central processing unit (CPU). Examples of the storage medium encompass a "non-transitory tangible medium" such as a read only memory (ROM), a tape, a disk, a card, a semiconductor memory, and a programmable logic circuit. The computer may further include a random access memory (RAM) or the like in which the program is loaded. The program can be made available to the computer via any transmission medium (such as a communication network or a broadcast wave) which allows the program to be transmitted. Note that an aspect of the present invention can also be achieved in the form of a computer data signal in which the program is embodied via electronic transmission and which is embedded in a carrier wave.

OTHER REMARKS

The present invention can be described also as follows.

In order to attain the above object, a safety verification system in accordance with an aspect of the present invention includes: at least one first sensor which is provided in a residential building and which detects, without contact, at least a heart rate and a respiratory rate of a resident of the residential building; a storage section which stores sensing data of the at least one first sensor; a detecting section which makes a comparison between the sensing data stored in the storage section and new sensing data of the at least one first sensor for detecting significant differences at least in the heart rate and the respiratory rate of the resident from a normal state; a communication section which carries out communication between the residential building and a facility away from the residential building; a notifying section which is provided in the facility and which notifies an operator in the facility of an occurrence of an anomaly via the communication section; an alerting section which causes, via the communication section, the notifying section to raise an alert when the detecting section has detected the significant differences; a safety verifying section which carries out, via the communication section, communication between the operator and the resident for verifying safety; a physiological information presenting section which is provided in the facility and which obtains at least the significant differences via the communication section and present at least the significant differences to the operator; an arrival information presenting unit which presents, to the operator, arrival of an emergency medical worker at the residential building in response to a dispatching request by the operator; and an unlocking unit which carries out, in response to an unlocking request by the operator, emergency unlocking of a lock that is provided at an entrance of the residential building.

According to the above configuration, the sensor provided in the residential building where a resident lives senses the state of the resident. From sensing data, the presence/absence of an anomaly of the resident is determined, and, if it is determined that there is an anomaly, an operator verifies the safety of the resident. If the safety of the resident cannot be confirmed, emergency help is requested. When an emergency medical worker has arrived at the residential building of the resident, the operator makes confirmation, and then the lock that is provided at the entrance of the residential building is unlocked. This makes it possible to quickly discover an anomaly of the resident in the house and, because of the verification of the safety by the operator, makes it possible to prevent an unnecessary request for emergency help. Furthermore, because the operator verifies whether or not it is the emergency medical worker who has arrived at the residential building of the resident, it is possible to prevent a case where the lock provided at the entrance of the residential building is unlocked even though it is not an emergency medical worker who has arrived. With the above configuration, it is thus possible to precisely determine an anomaly of a resident and handle the occurrence of the anomaly more safely, more reliably, and quickly.

The safety verification system in accordance with an aspect of the present invention can be configured so that the arrival information presenting unit includes: an image capturing section which captures an image or a video of the emergency medical worker who has arrived; an arrival information presenting section which obtains, via the communication section, the video or the image captured by the image capturing section; and a display section which displays, to the operator, the video or the image obtained by the arrival information presenting section.

With the above configuration, by confirming the video or the image, the operator can easily and clearly recognize whether or not it is the emergency medical worker who has arrived at the residential building.

The safety verification system in accordance with an aspect of the present invention can be configured so that the unlocking unit includes a remote unlocking section which unlocks the lock via the communication section by an operation of the operator.

With the above configuration, the lock of the residential building can be remotely unlocked by an operation of the operator.

The safety verification system in accordance with an aspect of the present invention can be configured to further include: a second sensor which is provided in the residential building and which detects that the resident has fallen in the residential building and detects, without contact, presence/absence of a subsequent movement of the resident who has fallen; and a fall determining section which, on the basis of sensing data of the second sensor, determines whether or not the resident is in a fallen state.

With the above configuration, it is possible to determine whether or not the resident has fallen and whether or not the resident is in the fallen state. This makes it possible to more clearly determine the presence/absence of an anomaly of the resident.

The safety verification system in accordance with an aspect of the present invention can be configured so that the at least one first sensor includes a plurality of first sensors which are provided in respective rooms in the residential building, the safety verification system further including: a diagram data storage section which stores diagram data that shows a floor plan of the residential building and shows an arrangement of the plurality of first sensors; and a transmitting section which transmits, to a mobile terminal carried by the emergency medical worker, guidance information that is based on sensing data of the plurality of first sensors and on the diagram data and that guides to a room where the resident having the significant differences detected is located.

With the above configuration, it is possible to quickly guide an emergency medical worker to the location of the resident. It is undesirable to waste time in searching for the resident because the location of the resident in the residential building is not identified even though the emergency medical worker has arrived at the residential building. In particular, in a situation where the resident requires urgent care, if it takes a long time for an emergency medical worker to get to the actual location of the resident after arriving at the residential building of the resident, it puts the resident's life at risk. With the above configuration, it is possible to make such a situation less likely.

The safety verification system in accordance with an aspect of the present invention can be configured so that the guidance information is indicative, on the floor plan of the residential building, of a route from the entrance of the residential building to a location of the resident having the significant differences detected.

With the above configuration, an emergency medical worker can easily recognize the route to the location of the resident having the significant differences detected.

In order to attain the above object, a safety verification method in accordance with an aspect of the present invention includes: a sensing step of causing a first sensor, which is provided in a residential building, to detect, without contact, at least a heart rate and a respiratory rate of a resident of the residential building; a storing step of storing sensing data of the first sensor in a storage section; a detecting step of making a comparison between the sensing data stored in the storing step and new sensing data of the first sensor for detecting significant differences at least in the heart rate and the respiratory rate of the resident from a normal state; an alerting step of, when the significant differences are detected in the detecting step, causing a notifying section, which is provided in a facility away from the residential building and which notifies an operator in the facility of an occurrence of an anomaly, to raises an alert; a safety verifying step of verifying the safety via a communication section which carries out communication between the operator and the resident in the residential building; a physiological information presenting step of obtaining at least the significant differences via the communication section and presenting at least the significant differences to the operator; an arrival information presenting step of presenting, to the operator, arrival of an emergency medical worker at the residential building in response to a dispatching request by the operator; and an unlocking step of carrying out, in response to an unlocking request by the operator, emergency unlocking of a lock that is provided at an entrance of the residential building.

A safety verification system in accordance with each aspect of the present invention can be realized by a computer. The computer is operated based on (i) a control program for causing the computer to realize the safety verification system by causing the computer to operate as each section (software element) included in the safety verification system and (ii) a computer-readable storage medium in which the control program is stored. Such a control program and a computer-readable storage medium are included in the scope of the present invention.

The present invention is not limited to the embodiments, but can be altered by a skilled person in the art within the scope of the claims. The present invention also encompasses, in its technical scope, any embodiment derived by combining technical means disclosed in differing embodiments.

REFERENCE SIGNS LIST

1 Safety verification system
10 House (residential building)
15 Resident
20 Management device
25 Operator
30 Emergency medical service
35 Emergency medical worker
100, 200 Control section
101 Information managing section
102 Door control section
110 Transmission/reception section
111 Sensor (111a: first sensor, 111b: second sensor)
120 Safety verification device
130 Camera (image capturing section)
140 Unlocking section
201 Anomaly determining section (fall determining section, detecting section)
202 Storage section
203 Remote unlocking section
204 Alerting section
205 Physiological information presenting section
206 Arrival information presenting section
207 Safety verifying section
210 Communication section (transmitting section)
220 Display section (notifying section)
230 Audio input/output section
240 Operation receiving section
400 Mobile terminal

The invention claimed is:

1. A safety verification system comprising:
at least one first sensor which is provided in a residential building and which detects, without contact, at least a heart rate and a respiratory rate of a resident of the residential building;
a storage section which stores sensing data of the at least one first sensor;
a detecting section which makes a comparison between the sensing data stored in the storage section and new sensing data of the at least one first sensor for detecting significant differences at least in the heart rate and the respiratory rate of the resident from a normal state;
a communication section which carries out communication between the residential building and a facility away from the residential building;
a notifying section which is provided in the facility and which notifies an operator in the facility of an occurrence of an anomaly via the communication section;
an alerting section which causes, via the communication section, the notifying section to raise an alert when the detecting section has detected the significant differences;

a safety verifying section which carries out, via the communication section, communication between the operator and the resident for verifying safety;

a physiological information presenting section which is provided in the facility and which obtains at least the significant differences via the communication section and present at least the significant differences to the operator;

an arrival information presenting unit which presents, to the operator, arrival of an emergency medical worker at the residential building in response to a dispatching request by the operator; and an unlocking unit which carries out, in response to an unlocking request by the operator, emergency unlocking of a lock that is provided at an entrance of the residential building.

2. The safety verification system according to claim 1, wherein the arrival information presenting unit includes: an image capturing section which captures an image or a video of the emergency medical worker who has arrived; an arrival information presenting section which obtains, via the communication section, the video or the image captured by the image capturing section; and a display section which displays, to the operator, the video or the image obtained by the arrival information presenting section.

3. The safety verification system according to claim 1, wherein
the unlocking unit includes
a remote unlocking section which unlocks the lock via the communication section by an operation of the operator.

4. The safety verification system according to claim 1, further comprising:
a second sensor which is provided in the residential building and which detects that the resident has fallen in the residential building and detects, without contact, presence/absence of a subsequent movement of the resident who has fallen; and
a fall determining section which, on the basis of sensing data of the second sensor, determines whether or not the resident is in a fallen state.

5. The safety verification system according to claim 1, wherein
the at least one first sensor comprises a plurality of first sensors which are provided in respective rooms in the residential building,
the safety verification system further comprising:
a diagram data storage section which stores diagram data that shows a floor plan of the residential building and shows an arrangement of the plurality of first sensors; and a transmitting section which transmits, to a mobile terminal carried by the emergency medical worker, guidance information that is based on sensing data of the plurality of first sensors and on the diagram data and that guides to a room where the resident having the significant differences detected is located.

6. The safety verification system according to claim 5, wherein
the guidance information is indicative, on the floor plan of the residential building, of a route from the entrance of the residential building to a location of the resident having the significant differences detected.

7. A method for verifying safety, comprising:
a sensing step of causing a first sensor, which is provided in a residential building, to detect, without contact, at least a heart rate and a respiratory rate of a resident of the residential building;
a storing step of storing sensing data of the first sensor in a storage section;
a detecting step of making a comparison between the sensing data stored in the storing step and new sensing data of the first sensor for detecting significant differences at least in the heart rate and the respiratory rate of the resident from a normal state;
an alerting step of, when the significant differences are detected in the detecting step, causing a notifying section, which is provided in a facility away from the residential building and which notifies an operator in the facility of an occurrence of an anomaly, to raises an alert;
a safety verifying step of verifying the safety via a communication section which carries out communication between the operator and the resident in the residential building;
a physiological information presenting step of obtaining at least the significant differences via the communication section and presenting at least the significant differences to the operator;
an arrival information presenting step of presenting, to the operator, arrival of an emergency medical worker at the residential building in response to a dispatching request by the operator; and
an unlocking step of carrying out, in response to an unlocking request by the operator, emergency unlocking of a lock that is provided at an entrance of the residential building.

\* \* \* \* \*